(12) United States Patent
Boebel et al.

(10) Patent No.: US 9,220,525 B2
(45) Date of Patent: Dec. 29, 2015

(54) MEDICAL INSTRUMENT HAVING ACTUATION ELEMENT MOVABLE INTO AT LEAST TWO POSITIONS

(75) Inventors: Manfred Boebel, Bauschlott (DE);
Stephan Prestel, Rheinstetten-Mörsch (DE); Eberhard Körner, Knittlingen (DE); Ernst Falk, Sternenfels-Diefenbach (DE)

(73) Assignee: Richard Wolf GmbH, Knittlingen (DE)

(*) Notice: Subject to any disclaimer, the term of this patent is extended or adjusted under 35 U.S.C. 154(b) by 227 days.

(21) Appl. No.: 12/913,813

(22) Filed: Oct. 28, 2010

(65) Prior Publication Data

US 2011/0106143 A1 May 5, 2011

(30) Foreign Application Priority Data

Oct. 31, 2009 (DE) .................. 10 2009 051 515

(51) Int. Cl.
*A61B 17/00* (2006.01)
*A61B 17/29* (2006.01)

(52) U.S. Cl.
CPC ....... *A61B 17/29* (2013.01); *A61B 2017/00367* (2013.01); *A61B 2017/00393* (2013.01); *A61B 2017/2904* (2013.01); *A61B 2017/2929* (2013.01); *A61B 2017/2946* (2013.01)

(58) Field of Classification Search
CPC .............. A61B 2017/2902; A61B 2017/2903; A61B 2017/2912; A61B 2017/2929; A61B 2017/2932; A61B 17/29; A61B 17/2909; A61B 17/320016; A61B 2017/292; A61B 2017/2923; A61B 2017/00367; A61B 2017/00389; A61B 2017/00393
USPC ....................... 606/205–209, 51–52
See application file for complete search history.

(56) References Cited

U.S. PATENT DOCUMENTS

| 5,174,300 | A | * | 12/1992 | Bales et al. | .................... 600/564 |
| 6,257,351 | B1 | * | 7/2001 | Ark et al. | ....................... 173/178 |
| 2003/0236549 | A1 | * | 12/2003 | Bonadio et al. | ................ 606/205 |

(Continued)

FOREIGN PATENT DOCUMENTS

| DE | 19647761 C1 * | 1/1998 | ............. G02B 23/24 |
| DE | 19630324 B4 | 5/2006 | |

(Continued)

OTHER PUBLICATIONS

Office Action issued on Aug. 23, 2010 in German Appln. Ser. No. 10 2009 051.515.1-35.
Office Action issued Jul. 4, 2012 in CN Application No. 201010534971.6.

*Primary Examiner* — David C Eastwood
*Assistant Examiner* — Martin T Ton
(74) *Attorney, Agent, or Firm* — Panitch Schwarze Belisario & Nadel LLP

(57) ABSTRACT

A medical instrument includes a handle on the proximal end and a shank rotatably arranged on the handle. A tool is arranged on the distal end of the shank. This tool is rotatable relative to the shank. An actuation element is arranged on the handle. The actuation element may be moved into at least two switch positions, wherein in a first switch position the actuation element is coupled in movement to the shank and in a second switch position the actuation element is coupled in movement to the tool.

10 Claims, 11 Drawing Sheets

(56) References Cited

U.S. PATENT DOCUMENTS

2007/0175947 A1* 8/2007 Ortiz et al. ................. 227/175.1
2009/0240274 A1* 9/2009 Boebel et al. ................. 606/174

FOREIGN PATENT DOCUMENTS

DE 102008015418 A1 9/2009
EP 2532315 A1 * 12/2012

* cited by examiner

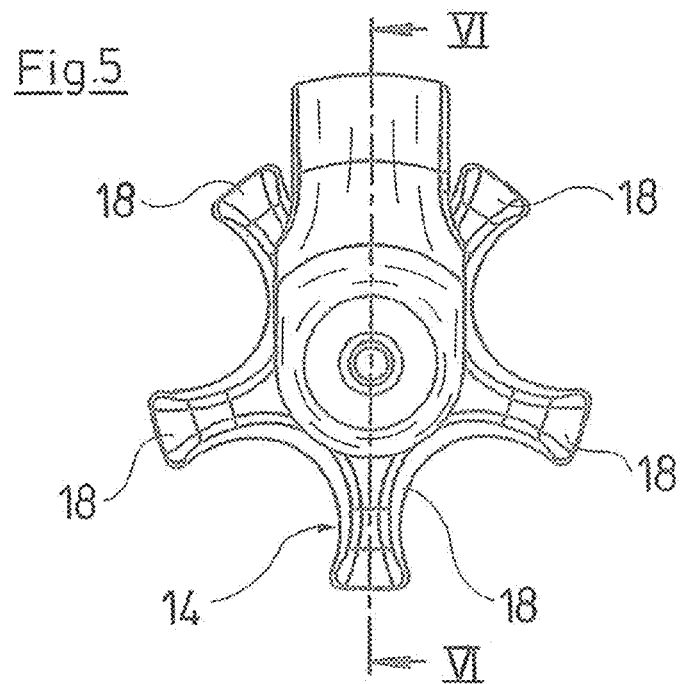
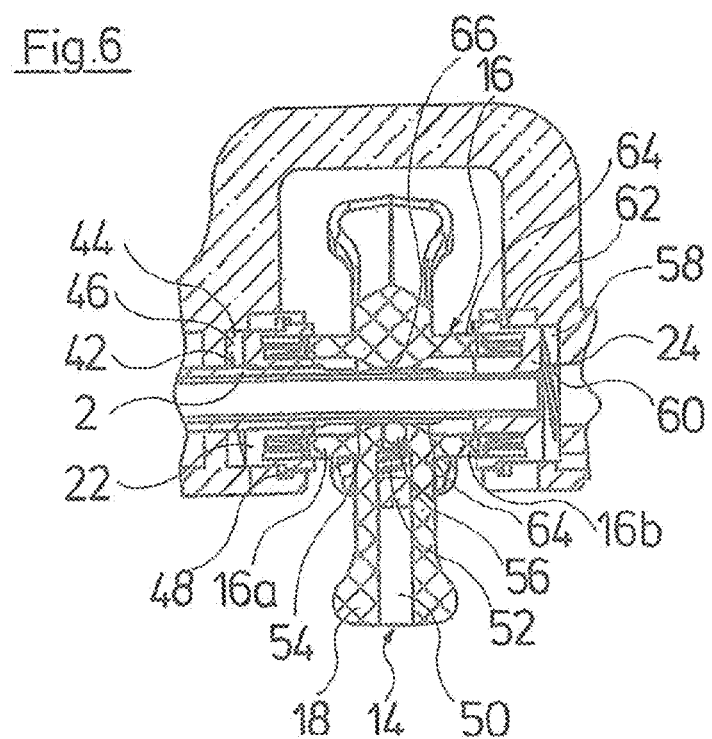

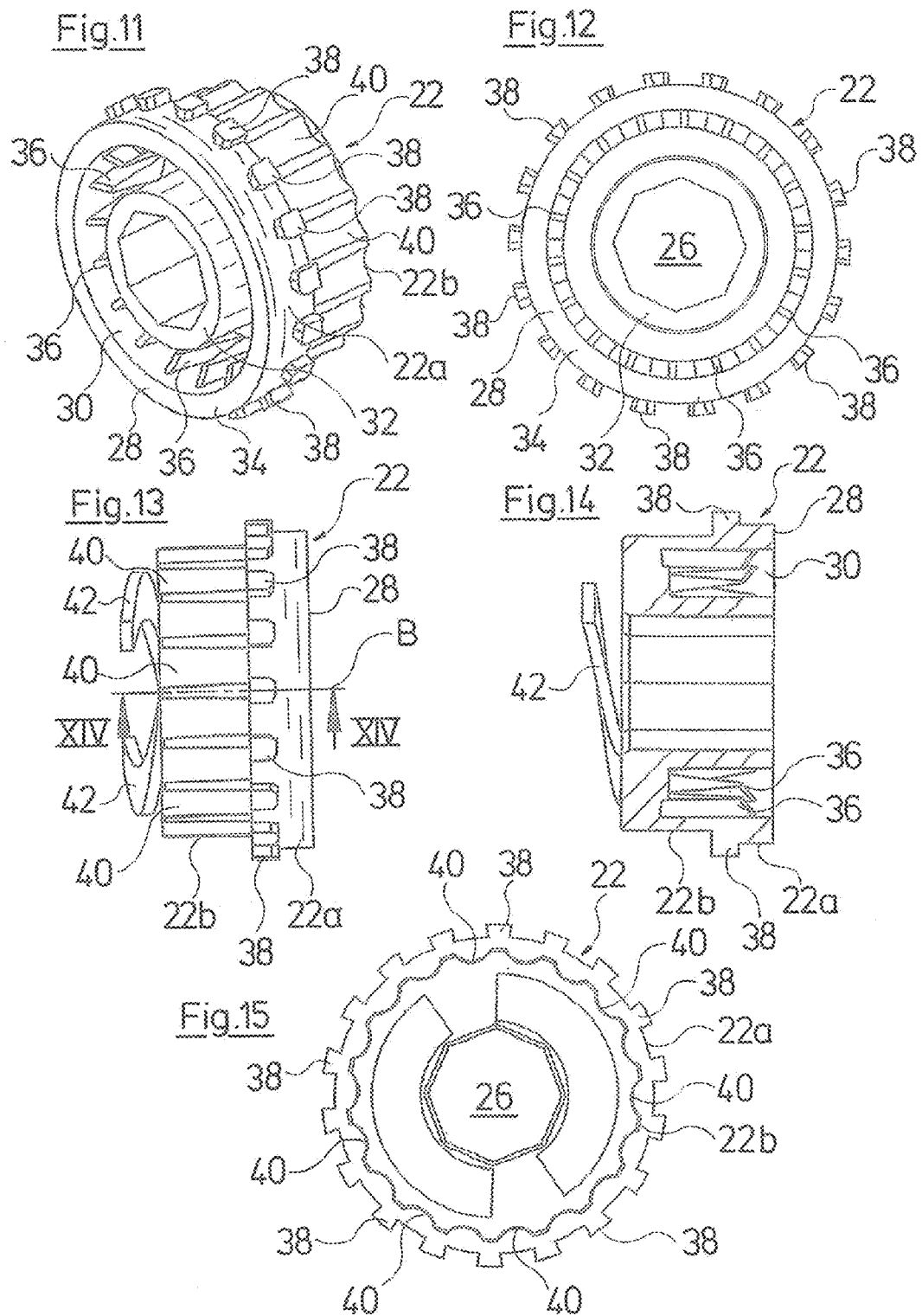

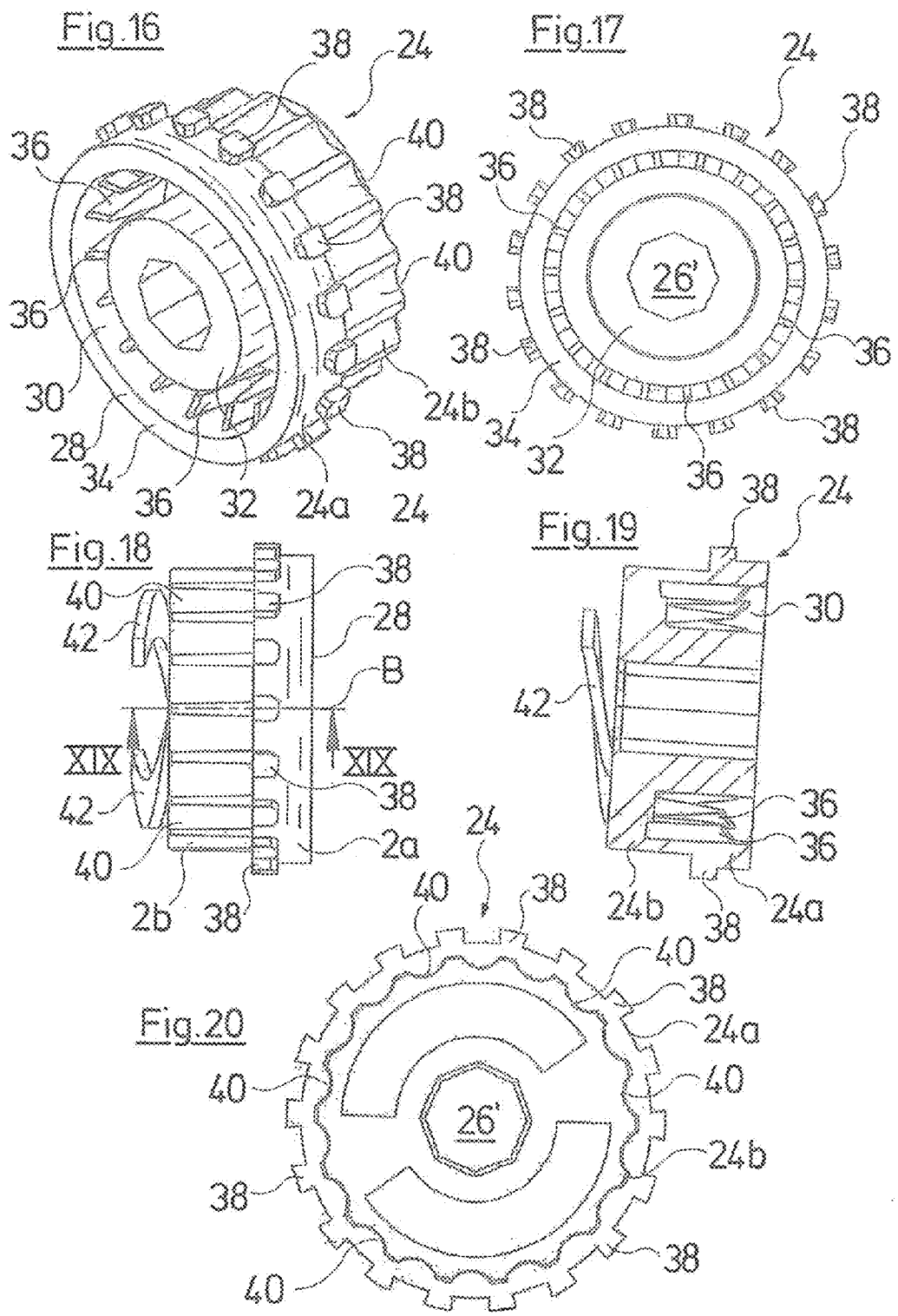

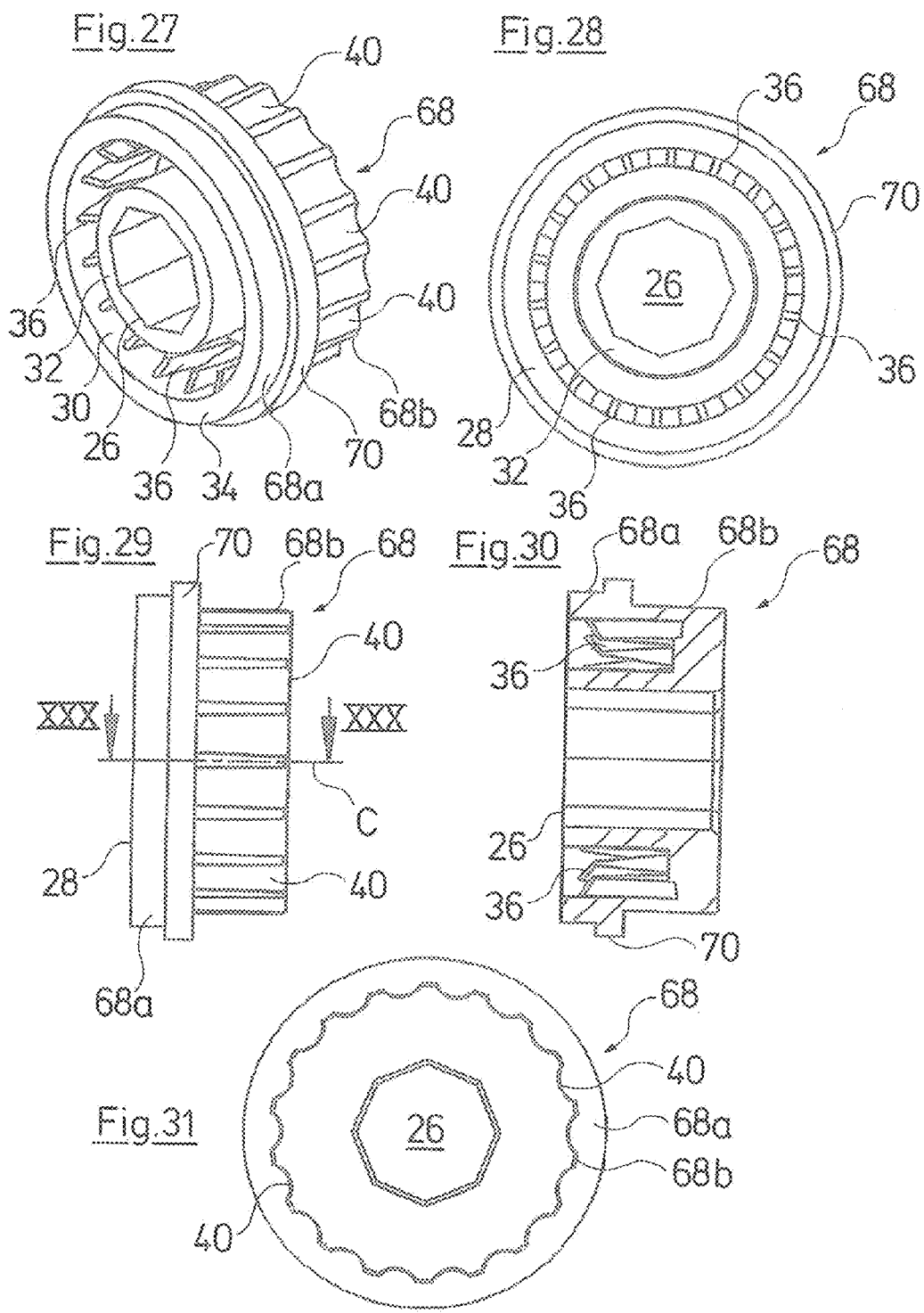

MEDICAL INSTRUMENT HAVING ACTUATION ELEMENT MOVABLE INTO AT LEAST TWO POSITIONS

BACKGROUND OF THE INVENTION

The invention relates to a medical instrument having a handle arranged on the proximal end, a shank rotatably arranged on the handle, and a tool arranged at the distal end of the shank and being rotatable relative to the shank.

An endoscopic instrument is known from German published patent application DE 10 2008 015 418 A1, which on the distal end of a handle comprises a shank with a bent distal end section, wherein forceps jaw parts or scissors jaw parts are selectively arranged at the distal shank end. With this instrument, the shank is rotatable relative to a longitudinal axis of the shank. The rotation ability of the shank permits the pivoting of the distal shank section away from the operating object, in order to create larger free spaces in the operation region.

For rotating the shank, this is coupled in movement to a rotation wheel arranged on the handle. Moreover, the forceps jaw or scissors jaw is also rotatable relative to the distal end section of the shank. For this, a second rotation wheel movably coupled to the jaw is provided on the handle. The two rotation wheels have a common rotation axis and are arranged spaced from one another on the handle with respect to this rotation axis. A first rotation wheel arranged on the proximal end is operated with the thumb by a person holding the instrument, and a rotation wheel which is distally spaced from this is operated with the index finger. Here, it has been found to be problematic that the rotation wheel operated by the thumb must be encompassed by the index finger with the operation of the rotation wheel spaced distally therefrom, whereby the rotation wheel on the proximal end may be undesirably moved. A further disadvantage of this instrument is to be seen in the fact that it impedes the application of two rotation wheels arranged behind one another on the handle, and the adaptation of the handle to different hand sizes of as many users of the instrument as possible.

BRIEF SUMMARY OF THE INVENTION

Against this background, it is the object of the invention to create a medical instrument of the previously described type, which permits a more ergonomic handling, even with different hand sizes of the user.

This object is achieved by a medical instrument of the type described at the outset, wherein an actuation element is arranged on the handle and is movable into at least two switch positions, wherein the actuation element is coupled in movement to the shank in a first switch position and to the tool in a second switch position. Advantageous further designs of this instrument are to be deduced from the following description as well as the drawings. Here, according to the invention, the features described may form the inventive solution respectively on their own, but also in combination.

The medical instrument according to the invention on the proximal end comprises a handle and a shank which is rotatably arranged on the handle. With regard to the shank, it is preferably a shank with which a distal end section is bent obliquely to the longitudinal axis of the shank in a proximal end section. A tool is arranged at the distal end of the shank. With regard to the tool, it may be a tool with a tool jaw, such as a forceps or scissors, a coagulation tool or the like. The tool may be rotated relative to the shank.

According to the invention, an actuation element is arranged on the handle, and may be moved into at least two switch positions, wherein in a first switch position it is coupled in movement to the shank, and in a second switch position it is coupled in movement to the tool. Designed in such a manner, the instrument according to an embodiment of the invention, with only one actuation element, allows the rotation of the shank of the instrument into a desired position relative to the handle of the instrument, as well as the rotation of the tool, arranged at the distal end of the shank, relative to the shank and relative to the handle. The actuation element may be arranged on the handle in a region, in which it may be comfortably operated by the users, independently of their hand size. Further advantageously, the actuation element, apart from the switch positions in which it is coupled to the shank or to the tool, may also be moved into at least one further switch position, in which the actuation element is neither coupled in movement to the shank nor to the tool, or may be moved into further switch positions, in order to carry out additional functions with the actuation element in these additional switch positions.

The actuation element is preferably rotatable respectively about a rotation axis, for the movement transmission onto the shaft or onto the tool. This means that depending on the switch position in which the actuation element is located, either the shank or the tool may be rotated by rotating the actuation element. Further preferably, the actuation element is axially displaceable into its switch positions in the direction of its rotation axis. Accordingly, the actuation element may be moved normally to the plane in which it may be rotated, into a position in which a movement coupling to the shank is effected, and into a further position in which a movement coupling to the tool is effected. As an actuation element, one may advantageously envisage a rotation wheel which may preferably be designed as a star wheel.

For the movement coupling the actuation element to the shank, the actuation element may advantageously comprise a first coupling part which forms a positive fit with a coupling part coupled in movement to the shank. Usefully, the first coupling part of the actuation element has such positive-fit means which, by a displacement of the actuation element in the direction of its rotation axis, may be brought into engagement with or disengaged from correspondingly formed positive fit means of the coupling part coupled in movement to the shank.

In order to also permit a movement transmission from the actuation element onto the tool in the second switch position of the actuation element, the actuation element may further advantageously comprise a second coupling part which forms a positive fit with a coupling part coupled in movement to the tool. In this case too, the second coupling part of the actuation element usefully has such positive-fit means which, by a displacement of the actuation element in the direction of its rotation axis, may engage into corresponding positive-fit means of the coupling part coupled in movement to the tool.

In a further advantageous design of the instrument according to the invention, the actuation element may comprise a spring-biased locking element, which in the first switch position of the actuation element engages into a first peripheral annular groove formed on the shank, and in the second switch position into a second peripheral annular groove formed on the shank. Thus preferably, a locking element may be arranged in the actuation element, in a manner such that it is pressed by the spring element radially in the direction of the shank and with a movement of the actuation element in the direction of its rotation axis, when reaching one of the two annular grooves formed on the shank on its outer periphery, engages into this annular groove. The annular grooves with this design are usefully arranged on the shank in a manner such that the actuation element is coupled in movement either to the shank or to the tool with the engagement of the locking element into one of the annular grooves. With the engagement of the locking element into the annular grooves, the actuation element is fixed in the axial direction with a non-positive or positive fit, either in the first or in the second switch position, wherein a rotation of the actuation element and thus a movement transmission from the movement element onto the shank or onto the tool is ensured. Unintended axial movements of the actuation element from the switch positions are advantageously prevented. If additional functions are to be carried out with the actuation element, or if the actuation element is to be fixed in a neutral position in which it carries out no function, then typically one may provide further annular grooves on the shank, into which the locking element may then engage.

Preferably, the first coupling part of the actuation element, with the coupling part coupled in movement to the shank, forms a first toothed coupling, and the second coupling part of the actuation element, with the coupling part coupled in movement to the shank, forms a second toothed coupling. For this, usefully a first toothed rim, provided with an outer toothing, forms the first coupling part of the actuation element, and a second toothed rim, provided with an outer toothing, forms the second coupling part of the actuation element.

In a manner corresponding to the first toothed rim of the actuation element, preferably a first hub with two ring sections spaced radially from one another is arranged on the shank, wherein a toothing corresponding to the toothing of the first toothed rim is formed in the inner side of an outer ring section of the two ring sections. By an axial movement of the actuation element in the direction of its rotation axis, the first toothed rim of the actuation element may be inserted into the intermediate space between the inner and the outer ring sections of the first hub, wherein the outer toothing formed on the first toothed rim of the actuation element comes into engagement with the inner toothing formed on the outer ring section of the first hub, so that a positive fit between the actuation element and the first hub, which is to say first coupling part coupled in movement to the shank, arises in the rotation direction of the actuation element.

Usefully, a hub which is coupled in movement to the tool and which forms a toothed coupling with the second toothed rim of the actuation element, is provided. This second hub is preferably arranged on a tube, on whose distal end the tool is arranged. The tube is usefully arranged in the shank in a rotationally movable manner. Advantageously, the second hub likewise comprises two ring sections which are radially spaced from one another, wherein a toothing corresponding to the toothing of the second toothed rim is formed on the inner side of the outer ring section.

Particularly advantageously, the teeth of the first toothed rim taper in the axial direction to the coupling part coupled in movement to the shank, and the teeth of the second toothed rim taper in the axial direction to the coupling part coupled in movement to the tool. Accordingly, the radially outwardly projecting teeth of the two toothed rims have a wedge-like shape in the direction of the rotation axis of the actuation element, this shape simplifying the engagement into the toothing of the coupling part coupled in movement to the shank or of the coupling part coupled in movement with the tool.

For the movement coupling of the first hub to the shank, the shank, advantageously in the region in which the first hub is arranged, has an outer cross-sectional contour with at least one straight flattened section, wherein the inner cross-sectional contour of the first hub, which delimits the inner ring section, corresponds to the outer cross-sectional contour of the shank. In this manner, a positive-fit is created in the rotation plane of the shank and the first hub, between the shank and the first hub. Preferably, the shank, in the region in which the first hub is arranged, has an octagonal outer cross section, and the first hub in a corresponding manner likewise has an octagonal inner cross section.

In order to fix the second hub on the tube guided in the shank, with positive fit in the rotation direction of the tube and the second hub, the tube guided in the shank, in the region in which the second hub is arranged on the tube, also preferably has an outer cross-sectional contour with at least one straight flattened section, wherein the inner cross-sectional contour of the second hub, which delimits the inner ring section, corresponds to the outer cross-sectional contour of the tube. Here too, one preferably envisages the tube, in the region in which the second hub is arranged, having an octagonal outer cross section, and the second hub having an octagonal inner cross section.

Advantageously, with the instrument according to an embodiment of the invention, the first coupling part which is coupled in movement to the shank, and the coupling part which is coupled to the tool, may be fixed on the handle against a rotational movement, when the respective coupling part is not coupled in movement to the actuation element. For this, both coupling parts may, for example, be displaceable in the displacement direction of the actuation element, wherein the coupling parts comprise positive-fit means, with which in one displacement position they are connectable to the handle in a rotationally fixed manner. In this displacement position, the coupling parts are advantageously pressed by a spring element which is arranged on the coupling parts. For rotating the first coupling part with the shank which is coupled in movement therewith, or for rotating the second coupling part coupled in movement to the tool, the respective coupling part may be displaced by the actuation element against the spring force of the spring element, into a position in which it is no longer fixed on the handle in a rotationally fixed manner, which means the positive fit of the respective coupling part with the handle is lifted by this.

Moreover, for the fixation of the two coupling parts in a rotationally locked manner, it is also possible to arrange these in the handle in a non-displaceable manner and to envisage a multitude of recesses on an outer side of the coupling parts, into which a handle-side locking element may engage with a non-positive and positive fit and thus secure the coupling parts against an unintended rotation. The force exerted by the locking element onto the coupling part is then to be overcome for rotating the coupling part.

BRIEF DESCRIPTION OF THE SEVERAL
VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawing are shown:

FIG. 5 is a front view of the actuation device according to FIG. 3;

FIG. 6 is a sectioned view of the actuation device according to FIG. 3, taken along the line VI-VI in FIG. 5;

FIG. 11 is a perspective representation of one embodiment of a hub of the actuation device according to FIG. 3;

FIG. 12 is a front view of the hub according to FIG. 11;

FIG. 13 is a lateral view of the hub according to FIG. 11;

FIG. 14 is a sectioned view taken along line XIV-XIV in FIG. 13;

FIG. 15 is a rear view of the hub according to FIG. 11;

FIG. 16 is a perspective representation of a second embodiment of a hub of the actuation device according to FIG. 3;

FIG. 17 is a front view of the hub according to FIG. 16;

FIG. 18 is a lateral view of the hub according to FIG. 16;

FIG. 19 is a sectioned view taken along the line XIX-XIX in FIG. 18;

FIG. 20 is a rear view of the hub according to FIG. 16;

FIG. 27 is a perspective representation of an embodiment of the hub of the actuation device according to FIG. 21;

FIG. 28 is a front view of the hub according to FIG. 27;

FIG. 29 is a side view of the hub according to FIG. 27;

FIG. 30 is a sectioned view taken along line XXX-XXX in FIG. 29; and

FIG. 31 is a rear view of the hub according to FIG. 27.

DETAILED DESCRIPTION OF THE INVENTION

Figure 1:
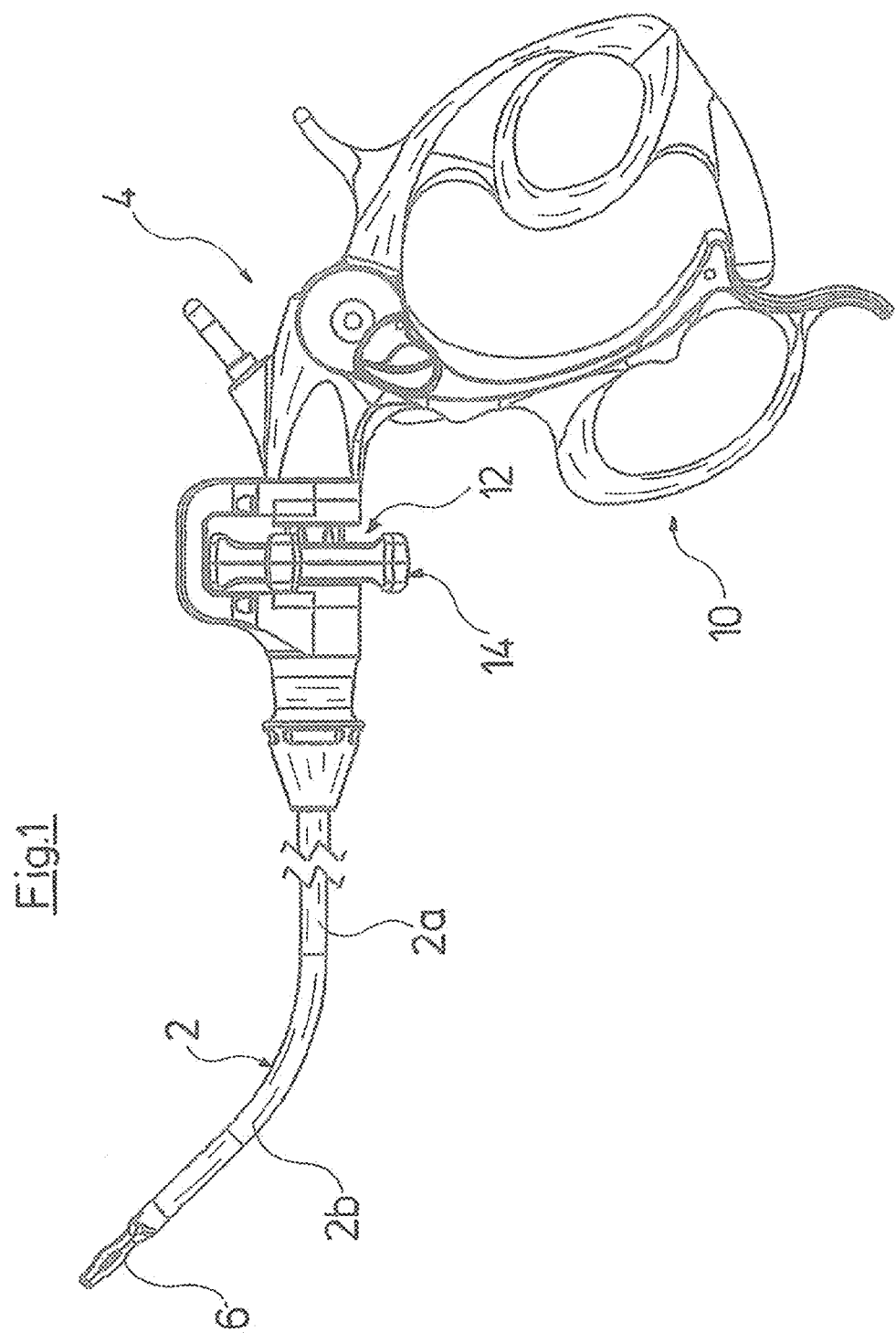
FIG. 1 is a schematic, lateral view of a medical instrument according to an embodiment of the invention.
Figure 2:
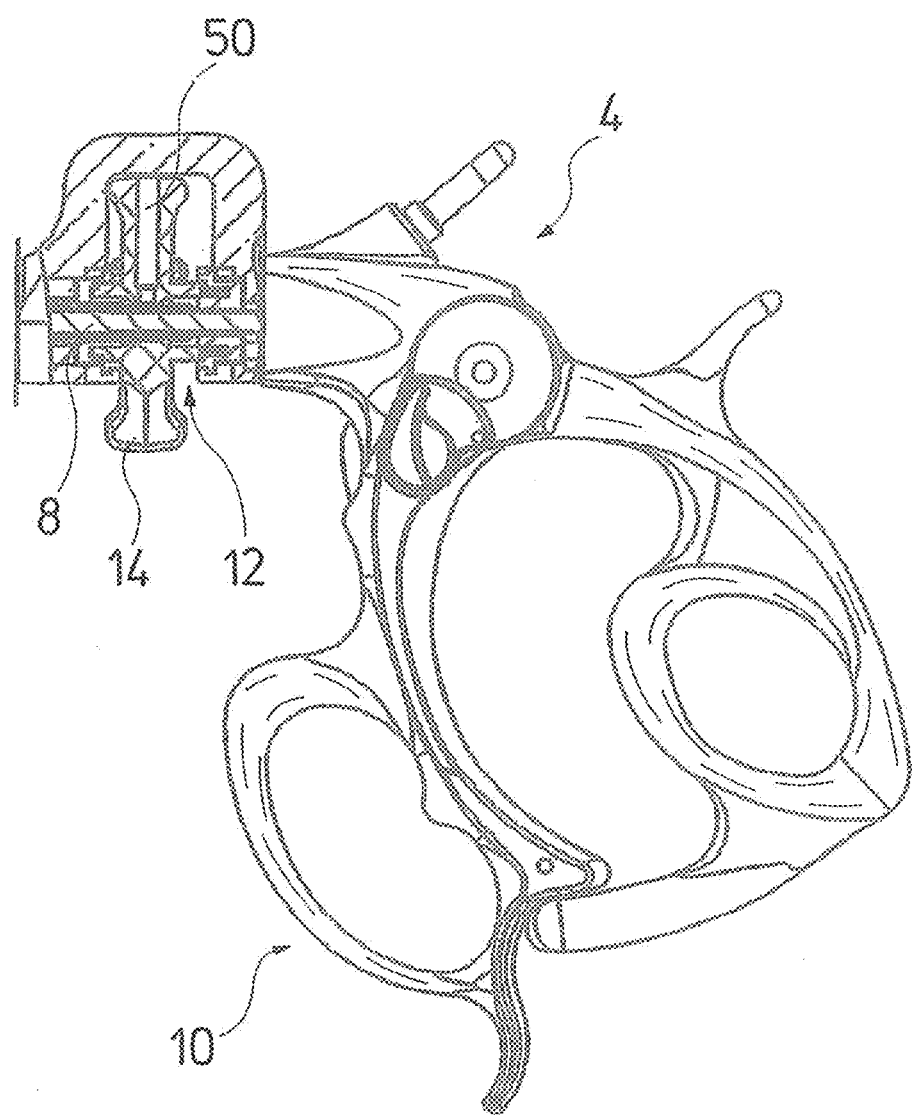
FIG. 2 is an enlarged, partly sectioned, lateral view of a handle of the instrument according to FIG. 1.
Figure 3:
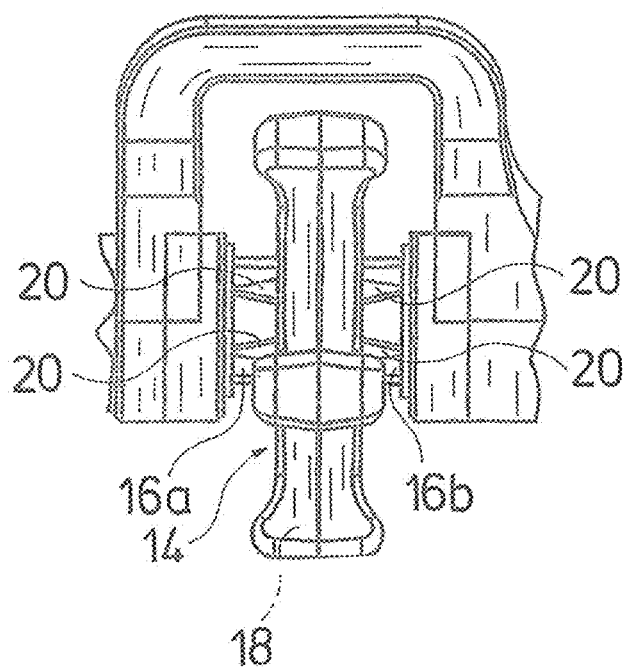
FIG. 3 is a perspective representation of a first embodiment of an actuation device for rotating a shank and a tool of the instrument according to FIG. 1.
Figure 4:
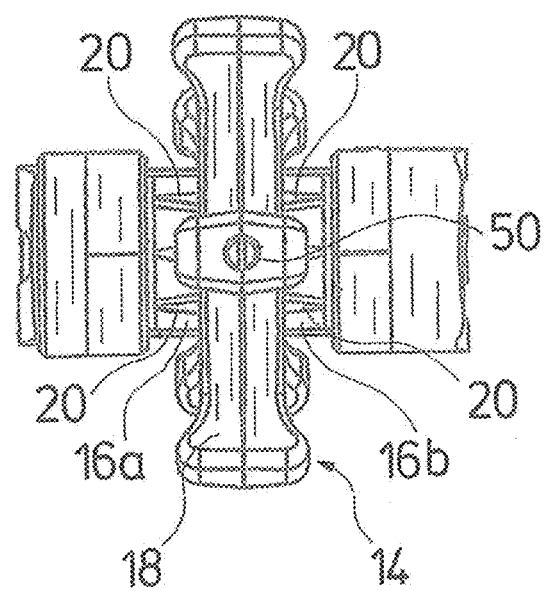
FIG. 4 is a bottom view of the actuation device according to FIG. 3.
Figure 7:
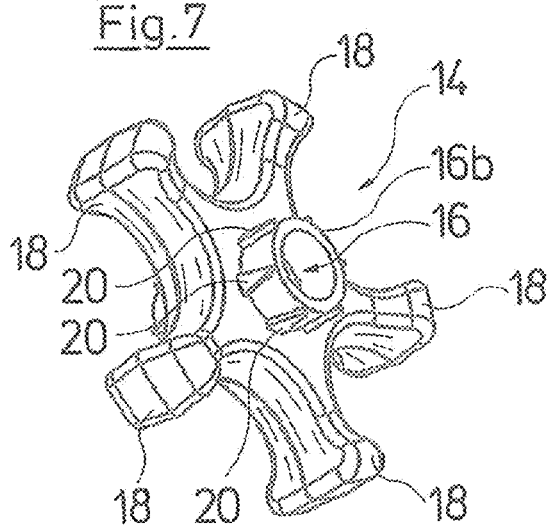
FIG. 7 is a perspective representation of an embodiment of an actuation element of the actuation device according to FIG. 3.
Figure 8:
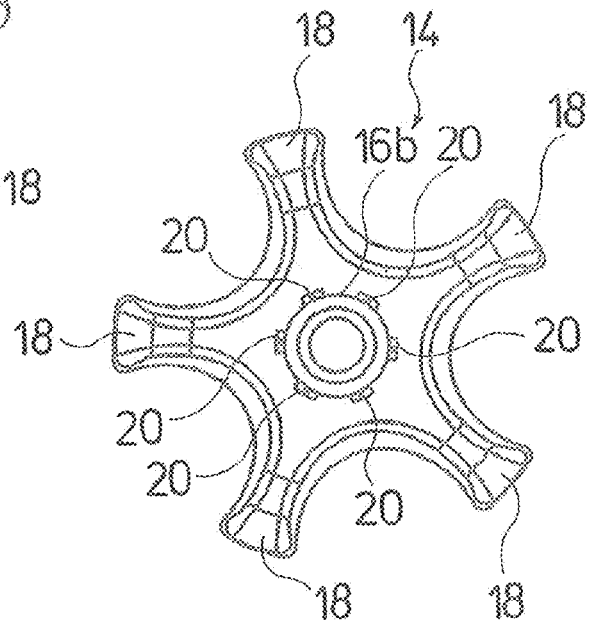
FIG. 8 is a front view of the actuation element according to FIG. 7.
Figure 9:
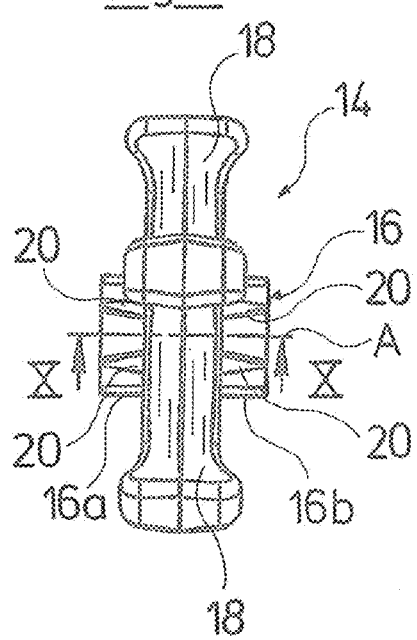
FIG. 9 is a lateral view of the actuation element according to FIG. 7.
Figure 10:
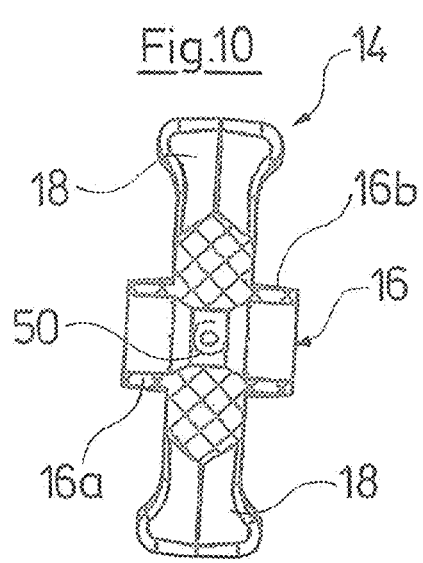
FIG. 10 is a sectioned view taken along the line X-X in FIG. 9.
Figure 21:
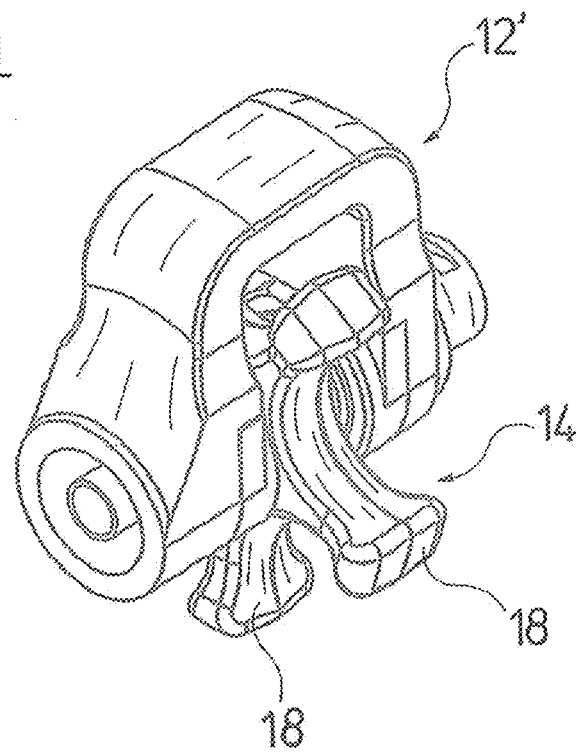
FIG. 21 is a perspective representation of a second embodiment of an actuation device for rotating a shank and a tool of the instrument according to FIG. 1.
Figure 22:
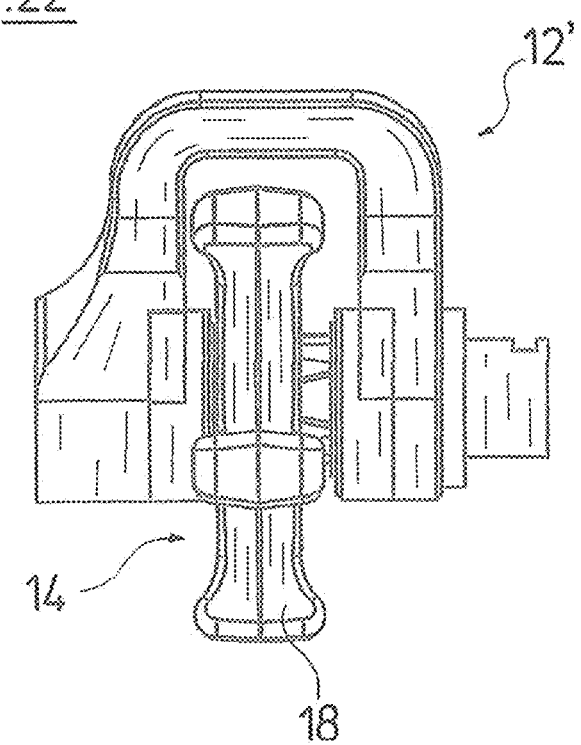
FIG. 22 is a lateral view of the actuation device according to FIG. 21.
Figure 23:
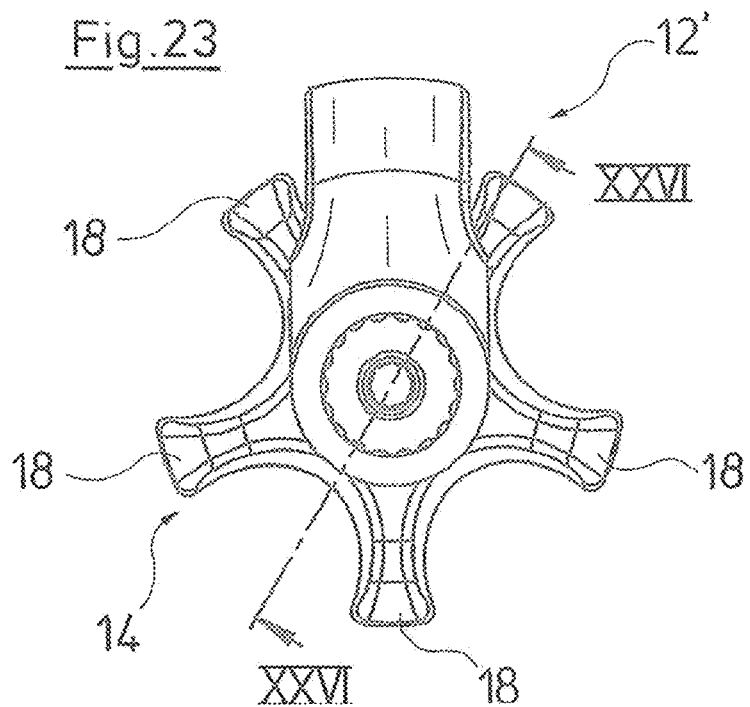
FIG. 23 is a front view of the actuation device according to FIG. 21.
Figure 24:
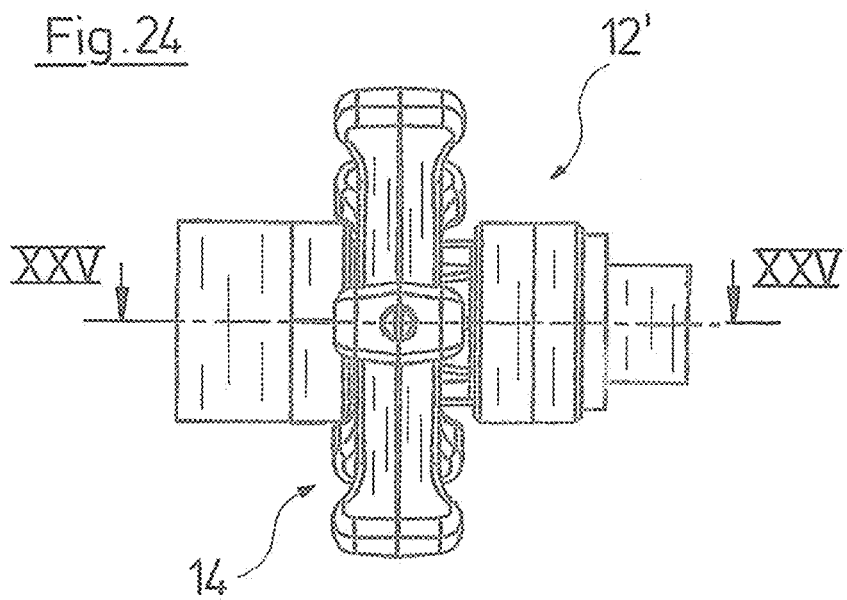
FIG. 24 is a view from below of the actuation device according to FIG. 21.

With the medical instrument represented in FIG. 1, there is a hollow shank instrument having a rigid shank 2, on which a handle 4 is arranged on the proximal end in the usual manner. The shank 2 has a straightly directed proximal shank section 2a (shown shortened) and a distal shank section 2b, which is bent obliquely to the shank section 2a and which connects thereto. A tool 6 in the form of a gripper forceps is arranged at the distal end section of the shank 2. The shank 2 is rotatably mounted in the handle 4 about the longitudinal axis of the proximal shank section 2a, and thus is rotatable relative to the handle 4. The tool 6 in turn is rotatable relative to the shank 2 and for this is fastened at the distal end of a tube 8 (FIG. 2), which is led through the shank 2. The tube 8 is rotatably mounted in the shank 2 and the handle 4.

The handle 4, for rotating the shank 2 and the tool 6, comprises an actuation device 12 between the grip part 10 and the distal end of the handle 4, at which end the shank 2 is led out of the handle 4. Such an actuation device 12 is represented in the FIGS. 3 to 6 in different views. The actuation device 12 comprises an operating element 14 for its manual operation. As may be particularly deduced from FIGS. 7 to 10, in which the operating element 14 is shown separately, a star wheel 14 forms the actuation element 14.

The star wheel 14 has a sleeve-like base body 16, on whose outer peripheral surface five actuation arms 18 distributed uniformly over its periphery project radially outward. Sections 16a and 16b of the base body 16, project in the direction of a longitudinal axis A of the star wheel 14 beyond the outer sides of the actuation arms 18. In each case, six teeth 20, which project radially outward, are formed on the peripheral surfaces of these sections 16a and 16b of the base body 16 and are distributed uniformly over the periphery of the sections 16a and 16b. Insofar as this is concerned, the sections 16a and 16b of the base body 16 form toothed rims 16a and 16b. The teeth 20 in the direction of the longitudinal axis A of the star wheel 14 have a wedge shape, wherein they taper respectively to the end-sides of the sections 16a and 16b of the base body 16.

The star wheel 14, in the actuation device 12, is rotatably mounted on the shank 2 rotatably guided there, and is displaceable on the shank 2 in a limited region in the direction of the longitudinal axis A of the star wheel 14 (FIG. 6). In the distal direction, the axial displacement path of the star wheel 14 is limited by a hub 22, which is arranged on the shank 2, while a hub 24, which is arranged on the tube 8 in a region which projects out of the shank 2, limits the displacement path of the star wheel 18 in the proximal direction.

The hub 22, which is represented separately in FIGS. 11 to 15, has an octagonal inner cross section 26. Correspondingly, the shank 2, in a region in which the hub 22 is to be arranged, has a corresponding octagonal outer cross section. A positive fit between the hub 22 and the shank 2 is created in the rotational direction of the shank 2, on account of this design of the inner cross section 26 of the hub 22 and of the outer cross section of the shank 2, so that the hub 22 may not rotate relative to the shank 2, and only a simultaneous rotation of the shank 2 and hub 22 is possible.

An annular groove 30 is formed on an end-side 28 of the hub 22 and is arranged concentrically to the inner cross section 26 of the hub 22. The annular groove 30 forms an inner ring section 32 and an outer ring section 34 which is radially spaced therefrom. A multitude of inwardly directed teeth 36 are arranged distributed uniformly over the inner periphery of the outer ring section 34, on the inner side of the outer ring section 34. The teeth 36 taper in a wedge-like manner in the direction of a longitudinal axis B of the hub 22 and in the direction of the end-side 28.

The outer cross section of the hub 22 is not constant. The hub 22 is designed in a stepped manner, with a first hub section 22a connecting to the end-side 28, whose outer diameter is larger than that of a hub section 22b connecting to the hub section 22a. A multitude of teeth 38 are arranged distributed uniformly over the periphery, on the outer periphery of the hub section 22a, where the hub section 22a merges into the hub section 22b. The teeth 38 project radially outward on the hub section 22a. A multitude of grooves 40 is formed on the hub section 22b. These grooves 40 extend over the whole periphery of the hub section 22b parallel to the longitudinal axis B of the hub 22. The grooves 40 have a concavely inwardly curved shape. Two leaf springs 42 are arranged at the end-side of the hub 22, this end-side facing away from the end-side 28, and this arrangement is such that the spring force of the springs is directed parallel to the longitudinal axis B of the hub 2.

The hub 24, which is represented separately in the FIGS. 16 to 20, differs from the hub 22 to the extent that the octagonal inner cross section 26' of the hub 24 is smaller than the inner cross section 26 of the hub 22. Otherwise, the hubs 22 and 24 correspond to one another in all other features.

The arrangement of the hub 22 on the shank 2 is to be deduced from FIG. 6. As has already been noted, the hub 22 is arranged on the shank 2 in a region in which the shank 2 has an octagonal outer cross section corresponding to the inner cross section 26 of the hub 22. This octagonal region of the shank 2 is longer than the dimension of the hub 22 in the direction of its longitudinal axis B, so that the hub 22 in this region may be axially displaced on the shank 2. The actuation device 12 comprises a recess 44 into which the hub 22 engages. Here, the leaf springs 42 of the hub 22 are supported on one of the end-faces 46 which delimit the recess 44. The outer toothing, which is formed by the teeth 38 on the outer periphery of the hub section 22a, is here in engagement with an inner toothing, which is correspondingly formed on the inner side of the recess 44. The hub 22 is thereby fixed with a positive fit against rotation about its longitudinal axis B. This means that in this position of the hub 22 the shank 2 may not be rotated.

For rotating the shank 2, the star wheel 14, which is arranged on the proximal end of the hub 22, is displaced in the direction of the hub 22, whereby the toothed rim 16a of the star wheel 14 engages into the annular groove 30, which is formed on the hub 22, and pushes the hub 22 against the spring force of the leaf springs 42 further into the recess 44. The outer toothing of the hub section 22a, this toothing formed by the teeth 38, is thereby pushed into an annular groove 48, which is formed on the recess behind the inner toothing in the displacement direction, so that the hub 22 may be rotated in this position. A bore 50, running in the radial direction and in which a locking element 52 is mounted, is formed in one of the actuation arms 18 of the star wheel 14, in order to be able to fix the hub 22, with the star wheel 14 which is engaged therein, in this position. A concavely inwardly curved annular groove 54 is formed on the shank 2. A ball 56 of the locking element 52 engages into this annular groove 54, when the hub 22 has been pushed by the star wheel 14 so far that the teeth 38 arranged on the hub section 22a are located in the annular groove 48 formed on the recess 44. The spring force exerted by the locking element 52 is sufficiently large that the spring force exerted by the leaf springs 42 is not sufficient to move the hub 22 out of this position. The shank 2 may be rotated in this position by rotating the star wheel 14, since the hub 22 and the star wheel 14 form a tooth coupling.

The hub 24 is arranged in the actuation device 12 on the proximal end of the star wheel 14 on a section 8 projecting out of the shank 2. In this section the tube 8 has an octagonal outer cross section, which corresponds to the inner cross section 26' of the hub 24. The hub 24 is axially displaceable in this section of the tube 8. A further recess 58 is formed in the actuation device 12, into which recess the hub 24 engages, whereby the leaf springs 42 of the hub 24 are supported on an end-face 60 delimiting the recess 58. The outer toothing, which is formed by the teeth 38 on the outer periphery of the hub section 24a, is here engaged with a corresponding inner toothing on the inner side of the recess 58. The hub 24 is thereby fixed with a positive fit against rotation about its longitudinal axis B, which means to say that the tube 8 may not be rotated in this position of the hub 24.

For rotating the tube 8, the star wheel 14, which is arranged on the distal end of the hub 24, is pushed in the direction of the hub 24, whereby the toothed rim 16b of the star wheel 14 engages into the annular groove 30 formed on the hub 24, and pushes the hub 24 further into the recess 58, against the spring force of the leaf springs 42. The outer toothing of the hub section 24a, this outer toothing being formed by the teeth 38, is thereby pushed into an annular groove 62, which is formed on a recess in front of the inner toothing in the displacement direction of the star wheel 14, so that the hub 24 is rotatable in this position.

A further concavely inwardly curved annular groove 64 is formed on the shank 2, corresponding to this position. The ball 56 of the locking element 52 arranged in the star wheel 14, engages into this annular groove 64, when the hub 24 has displaced so far from the star wheel 14, that the teeth 38 arranged in the hub section 24a are located in the annular groove 62 formed on the recess 44. The spring force exerted by the locking element 52 is sufficiently large that it exceeds the spring force exerted by the leaf springs 42, so that the spring force exerted by the leaf springs 42 is not sufficient to move the hub 24 out of this position. Since the hub 24 and the star wheel 14 form a toothed coupling, the tube 8 may be rotated in this position by rotation of the star wheel 14.

A further annular groove 66 is formed on the shank 2, between the annular grooves 54 and 64 formed on the shank 2. If the ball 56 of the locking element 52 engages into this annular groove 66, the star wheel 14 is held in a neutral position, in which it is neither in engagement with the hub 22 nor with the hub 24, so that neither the shank 2 nor the tool 6 arranged at the distal end of the tube 8 may be moved by a rotation of the star wheel 14.

An alternative actuation device 12' for rotating the shank 2 and the tool 6 is represented in the FIGS. 21 to 26. This actuation device 12' differs from the actuation device 12 described above essentially by the design of the hubs arranged on the shank 2 and the tube 8, which together with the star wheel 14 form toothed couplings for rotating the shank 2 or the tube 8, and by the arrangement of these hubs in the actuation device 12'.

A hub 68, which is shown separately in different views in the FIGS. 21 to 27, is arranged on the shank 2, in the actuation device 12'. The hub 68 differs from the hub 22 represented in FIGS. 11 to 15 by the fact that the outer toothing formed by the teeth 38 with regard to the hub 22, and the spring elements 42 arranged on the end-side of the hub section 22b with regard to the hub 22, are absent with the hub 68. Moreover, instead of the toothing formed on the hub section 22a of the hub 22, an annular projection 70 projects radially outward on a hub section 68a of the hub 68, and this hub section corresponds to the hub section 22a of the hub 22.

Figure 25:
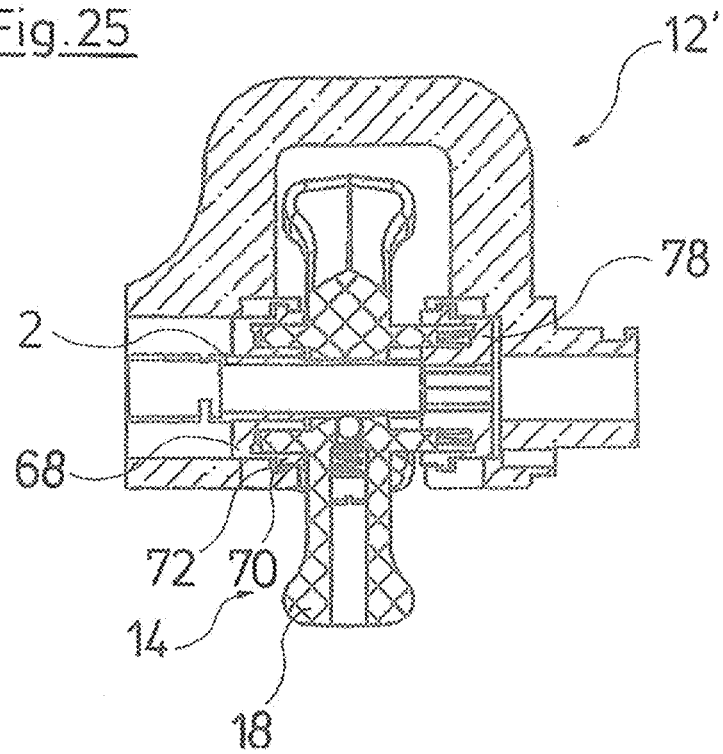
FIG. 25 is a sectioned view taken along line XXV-XXV in FIG. 24.
Figure 26:
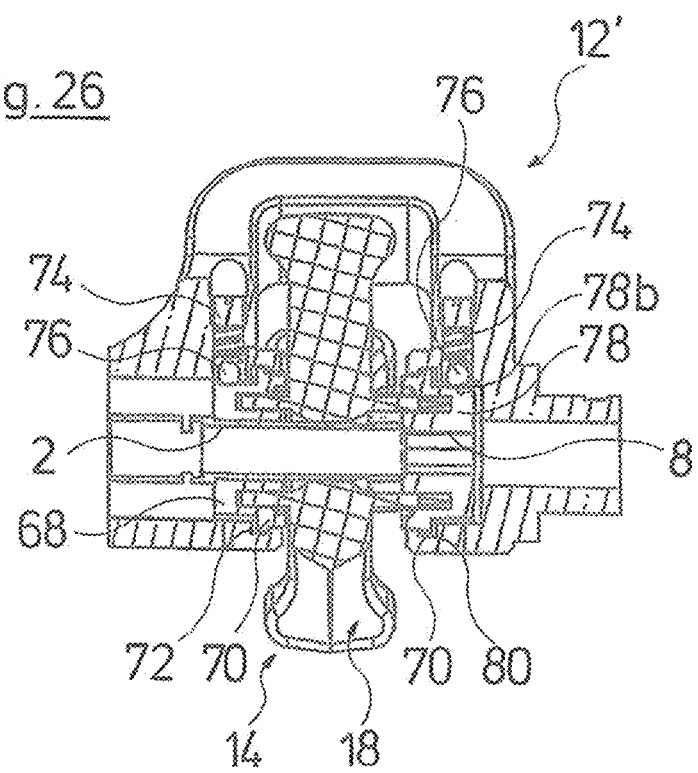
FIG. 26 is a sectioned view taken along line XXVI-XXVI in FIG. 23.

The arrangement of the hub 68 on the shank 2 in the actuation device 12' is to be deduced from FIGS. 25 and 26. The hub 68 is not arranged in a displaceable manner in the actuation device 12'. Instead, the projection 70 of the hub 68 engages into an annular groove 72, which is formed on the actuation device 12', and in this manner is secured against an axial movement with a positive fit. In order to secure the hub 68 or the shank 2 against unintended rotational movement, a locking element 74 is arranged in the actuation device 12' on the outer side of a hub section 68b, which corresponds to the hub section 22b of the hub 22, in a manner such that a locking ball 76 of the locking element 74 engages into the grooves 40 formed on the hub section 68b. As with the actuation device 12 represented in FIGS. 3 to 6, the engagement of the toothed rim 16a of the star wheel into the toothing formed on the hub 68, permits a movement coupling of the star wheel 14 to the hub 68 or to the shank 2, wherein here the spring force exerted by the locking element 74 must be overcome.

The design of the hub 78 arranged on the tube 8 in the actuation device 12' corresponds to the design of the hub 68, with the difference that the inner cross section of the hub 78 is adapted to the octagonal outer cross section of the tube 8. The hub 78 also is not displaceably arranged in the actuation device 12'. Instead of this, a projection 70 of the hub 78 engages into a further annular groove 80 formed on the actuation device 12' and is secured in this manner with a positive fit against an axial movement.

A further locking element 74 is arranged in the actuation device 12' on the outer side of a hub section 78, which corresponds to the hub section 68b of the hub 68, in a manner such that the locking ball 76 of this locking element 74 engages into the grooves 40 formed on the hub section 68b, in order to secure the hub 78 or the tube 8 against unintended rotational movement. As with the actuation device 12 represented in FIGS. 3 to 6, the engagement of the star wheel 14 into the toothing formed on the hub 78 permits a movement coupling of the star wheel 14 to the hub 78 or to the tube 8. The spring force exerted by the locking element 74 must be lifted for rotating the tube 8, whereby the locking ball 76 of the locking element 74 engages respectively into the groove 40, which is next in the rotation direction, and thus permits a stepped rotational movement.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A medical instrument comprising:
    a handle (4) arranged on a proximal end of the instrument,
    a shank (2) having a longitudinal axis and rotatably arranged on the handle (4), the shank (2) being rotatable about the longitudinal axis,
    a tool (6) arranged at a distal end of the shank (2), the tool being rotatable relative to the shank (2),
    a shank coupling part coupled in movement to the shank (2),
    a tool coupling part coupled in movement to the tool (6),
    an actuation element (14) arranged on the handle (4), wherein a single component of the actuation element (14) includes a first coupling part comprising a first toothed rim (16a) comprising an outer toothing and teeth tapering in an axial direction to the shank coupling part and a second coupling part comprising a second toothed rim (16b) comprising an outer toothing and teeth tapering in an axial direction to the tool coupling part, the actuation element being axially displaceable in a direction of the longitudinal axis between at least two switch positions, the first coupling part of the actuation element forming a positive fit with the shank coupling part coupled to the shank (2) in a first switch position and the second coupling part of the actuation element forming a positive fit with the tool coupling part coupled to the tool (6) in a second switch position, wherein the single component of the actuation element is rotatable about the longitudinal axis in each of the first and second switch positions such that the single component effects movement of the shank when in the first position and effects movement of the tool when in the second position, and
    a grip part (10) positioned proximal to the actuation element (14) along the longitudinal axis.

2. The medical instrument according to claim 1, wherein the actuation element (14) has a spring-biased locking element (52), which in the first switch position engages into a first peripheral annular groove (54) formed on the shank (2), and in the second switch position engages into a second peripheral annular groove (64) formed on the shank (2).

3. The medical instrument according to claim 1, further comprising a first hub (22, 68) having inner and outer ring sections (32, 34) radially spaced from one another, the first hub being arranged on the shank (2), wherein an inner side of the outer ring section (34) has a toothing corresponding to the toothing of the first toothed rim (16a).

4. The medical instrument according to claim 3, wherein the shank (2), in a region where the first hub (22, 68) is arranged, has an outer cross-sectional contour having at least one straight flattened section, and the first hub (22, 68) has an inner cross-sectional contour (26) delimited by an inner peripheral wall and corresponding to an outer cross-sectional contour of the shank (2).

5. The medical instrument according to claim 1, wherein the tool (6) is arranged on a distal end of a tube (8) guided in the shank (2) in a rotationally moveable manner, wherein a second hub (24, 78), having inner and outer ring sections (32, 34) radially spaced from one another, is arranged on the tube (8), and wherein an inner side of the outer ring section (34) has toothing corresponding to the toothing of the second toothed rim (16b).

6. The medical instrument according to claim 5, wherein in a region where the second hub (24, 78) is arranged on the tube (8), the tube has an outer cross-sectional contour having at least one straight, flattened section, and the second hub (24, 78) has an inner cross-sectional contour delimited by an inner peripheral wall (32) and corresponding to an outer cross-sectional contour of the tube (8).

7. The medical instrument according to claim 1, wherein the shank coupling part is displaceable in a displacement direction of the actuation element (14) and comprises positive fit means such that in one displacement position the shank coupling part is connectable in a rotationally fixed manner to the handle (4).

8. The medical instrument according to claim 1, wherein the tool coupling part is displaceable in a displacement direction of the actuation element (14) and comprises positive fit means such that in one displacement position the tool coupling part is connectable in a rotationally fixed manner to the handle (4).

9. The medical instrument according to claim 1, wherein the shank coupling part is not displaceable in a displacement direction of the actuation element (14) and comprises positive fit means into which a locking element (74) provided on the handle (4) engages.

10. The medical instrument according to claim 1, wherein the tool coupling part is not displaceable in a displacement direction of the actuation element (14) and comprises positive fit means into which a further locking element (74) provided on the handle engages.

* * * * *